US006867421B1

(12) United States Patent
Hunt et al.

(10) Patent No.: US 6,867,421 B1
(45) Date of Patent: Mar. 15, 2005

(54) IN-LINE PROCESS FOR MONITORING BINDER DOSAGE AND DISTRIBUTION ON A SURFACE AND APPARATUS USEFUL THEREFOR

(75) Inventors: Robert N. Hunt, Steubenville, OH (US); Terry L. Thiem, Brights Grove (CA)

(73) Assignee: Bayer Materialscience LLC, Pittsburgh, PA (US)

( * ) Notice: Subject to any disclaimer, the term of this patent is extended or adjusted under 35 U.S.C. 154(b) by 0 days.

(21) Appl. No.: 09/222,092

(22) Filed: Dec. 29, 1998

(51) Int. Cl.$^7$ .............................................. G01N 21/64
(52) U.S. Cl. ............................ 250/461.1; 250/458.1; 250/459.1
(58) Field of Search ........................ 250/461.1, 458.1, 250/459.1

(56) References Cited

U.S. PATENT DOCUMENTS

| | | | |
|---|---|---|---|
| 4,415,516 A | * 11/1983 | Krueger et al. | 264/112 |
| 4,651,011 A | 3/1987 | Ors et al. | 250/459.1 |
| 4,824,209 A | 4/1989 | Bolton et al. | 359/894 |
| 4,827,142 A | 5/1989 | Hatje | 250/559.25 |
| 4,885,254 A | 12/1989 | Sung | 436/85 |
| 4,891,530 A | 1/1990 | Hatji | 250/559.4 |
| 4,922,113 A | 5/1990 | Melancon | 250/372 |
| 5,100,802 A | 3/1992 | Mickols | 436/34 |
| 5,532,817 A | 7/1996 | DeVries et al. | 356/318 |
| 5,818,577 A | 10/1998 | Duclos et al. | 356/237.1 |
| 6,001,936 A | * 12/1999 | Barrera et al. | 525/454 |
| 6,007,649 A | 12/1999 | Haas et al. | 156/62.2 |

FOREIGN PATENT DOCUMENTS

EP     458 474     11/1991

OTHER PUBLICATIONS

Sun et al, Institute of Material Science, Storrs Report TR–38–ONR, Connecticut Univ. (Abstract attached) 1994.
F. Kamke's work reported in Wood Based Composites Program Annual Report (Jun. 1, 1994–May 31, 1995).

* cited by examiner

Primary Examiner—David Porta
Assistant Examiner—Shun Lee
(74) Attorney, Agent, or Firm—Joseph C. Gil; Lyndanne M. Whalen

(57) ABSTRACT

A method and apparatus for determining binder dosage and distribution on a substrate. The apparatus employed is made up of:
  a) a source of long wave ultraviolet light positioned so that ultraviolet waves emitted therefrom will come into contact with a substrate to which binder has been applied,
  b) a filter which blocks ultraviolet waves emitted from the UV source and reflected by the substrate but which allows visible light waves emitted by fluorescence of the binder to pass,
  c) a lens for imaging visible light onto a focal plane,
  d) a video camera positioned at the focal plane of the lens which converts the visible light waves that have passed through the filter and the lens into an electrical signal, and
  e) a device capable of correlating images received by the video camera to binder dosage and distribution on the substrate contacted by the ultraviolet waves emitted by the UV source.

1 Claim, 14 Drawing Sheets

IN-LINE PROCESS FOR MONITORING BINDER DOSAGE AND DISTRIBUTION ON A SURFACE AND APPARATUS USEFUL THEREFOR

BACKGROUND OF THE INVENTION

The present invention relates to a process for monitoring binder, particularly isocyanate-based binders, dosage and distribution on a surface by ultraviolet fluorescence and to apparatus useful therefor.

Various types of binders have been used to produce engineered composite materials such as oriented strand board. Suitable binders include phenol formaldehyde resins and isocyanates, particularly polymeric diphenylmethane diisocyanate ("PMDI"). In producing such engineered composites, the binder is generally applied to a material such as wood fibers, wood strands, wood flakes or some other lignocellulose-based material. Ideally, the amount of binder applied ("dosage") would be sufficient to cover 100% of the surface of 100% of the wood fibers, wood strands, etc. ("distribution"). In most commercial processes, an excess of binder is used to ensure sufficient distribution. Longer than necessary mixing times may also be used to ensure that the binder is sufficiently distributed so that weak spots in the composite material due to insufficient adhesion do not occur. This use of excess binder and extended mixing times significantly increases the cost of producing engineered composite materials.

It would therefore be advantageous to develop a method for determining binder dosage and distribution during the composite production process with sufficient accuracy that use of excess binder and extended mixing times are unnecessary.

Spectroscopic methods for making such determinations have been investigated by those seeking to improve the production of composite materials. Solid NMR characterization of the bonding of composite materials was studied by Frazier and Wendler and the results were presented in "15N CP/MAS NMR analysis of pMDI bonded cellulose composites" presented at the 48th Annual Meeting of the Forest Products Society, Portland, Me., Jun. 26–29, 1994. Sun et al attempted to correlate fluorescence intensity changes with FTIR spectra generated by monitoring the disappearance of the isocyanate group during the reaction which occurs in the commercial production process. (See, e.g., Sun et al, Institute of Materials Science, Storrs Report TR-38-ONR, Connecticut University (1994).)

UV absorption and fluorescence spectroscopy are also techniques which have been evaluated for their usefulness in monitoring urethane-forming reactions. However, until now, methods utilizing such UV spectroscopic techniques were not capable of providing real time, macroscopic imaging of the composite material as it was being produced.

For example, F. Kamke's work reported in "Wood Based Composites Program Annual Report" (Jun. 1, 1994–May 31, 1995) was a microscopic study of UV fluorescence imaging of polymeric MDI resin distribution on wood strands. Kamke states that because polymeric MDI fluorescence is very weak, a very intense UV source (specifically, a 100 watt mercury vapor lamp) and signal averaging of many video frames to reduce noise level were necessary. Although signal averaging to reduce noise level works well for stationary samples, it is not very useful when the material being evaluated is moving on a conveyor belt and the video image is constantly changing. Microscopic evaluation of a material is also impractical for monitoring a commercial production process because of the great potential for variation between samples. The Kamke method would not therefore be practical for monitoring a commercial process for the production of a composite material.

Yu et al report a technique in which naphthylene diisocyanate is used as a molecular sensor to monitor cure reactions in a polyurethane in U.S. Pat. No. 4,885,254. Yu et al correlate the fluorescence intensity and overall extent of reaction between 1,5-naphthyl diisocyanate and n-butanol. This correlation was established by identifying the various species present during the urethane-forming reaction using HPLC that was confirmed by IR spectra. The UV-visible absorption spectrum and fluorescence spectrum for each of these species were then generated. Shifts in the UV-visible spectrum were observed as the naphthyl diisocyanate reacted to form the monourethane and diurethane. The fraction of each species present at a given time was determined by linear regression analysis. The extent of the reaction was calculated from UV spectral analysis. A correlation between the experimentally determined fluorescence intensity at 357 nanometers and the calculated overall extent of reaction derived from UV spectral analysis was made.

U.S. Pat. No. 5,100,802 discloses a method for measuring the rate and extent of cure of a resin system in which a fluorescent dye is added to the system being polymerized.

U.S. Pat. No. 4,922,113 discloses a method for monitoring a coating's weight, uniformity and surface defects in which a UV-escer that absorbs radiant energy is included in the coating composition. The radiant energy emitted by the coating at the same wavelength as energy emitted by the UV-escer can be detected and correlated to pre-established standards.

U.S. Pat. No. 4,651,011 discloses a method for determining the extent of cure of a polymer. In this method, the degree of free space rotation of a fluorospore added to the polymer system is determined by fluorescent measurement of the fluorospore.

To date, however, no method for determining binder dosing, particularly isocyanate-based binder dosing and distribution during actual production of composite materials without adding some type of "marker" such as a dye, fluorospore or UV-escer has been developed.

SUMMARY OF THE INVENTION

It is an object of the present invention to provide an apparatus for determining binder dosage and distribution during the production of a composite material.

It is also an object of the present invention to provide an apparatus for determining binder dosage and distribution while the composite-forming material is moving, for example, on a conveyor belt.

It is another object of the present invention to provide an apparatus for accurately determining binder dosage and distribution during production of a composite from a composite-forming material that does not include a marker material such as a UV-escer, fluorospore or dye.

It is a further object of the present invention to provide an in-line monitoring process which is capable of detecting binder dosage and distribution with a high degree of accuracy even though the material being monitored is not stationary.

These and other objects of the present invention which will be apparent to those skilled in the art are accomplished by exposing the composite-forming material to long wave ultraviolet radiation to excite the binder molecules sufficiently to induce fluorescence and emission of visible radiation while passing the composite-forming material through the field of view of a video camera equipped with a suitable filter. The video camera is positioned to receive the visible fluorescence emitted by the binder molecules. The video camera is connected to a device capable of correlating the visible fluorescence collected to pre-established standards such as a computer programmed with an appropriate database.

DETAILED DESCRIPTION OF THE PRESENT INVENTION

The present invention is directed to an in-line process for monitoring binder, particularly isocyanate-based binder, dosage and distribution during the production of composite materials and to apparatus useful therefor.

The apparatus of the present invention is composed of a long wave ultraviolet radiation source, a filter or a set of filters, a lens, a video camera and a means for correlating the ultraviolet fluorescence data collected from a sample to the dosage and distribution of binder In that sample. A typical arrangement of these components of the apparatus of the present invention is shown in FIG. 1.

Figure 1:
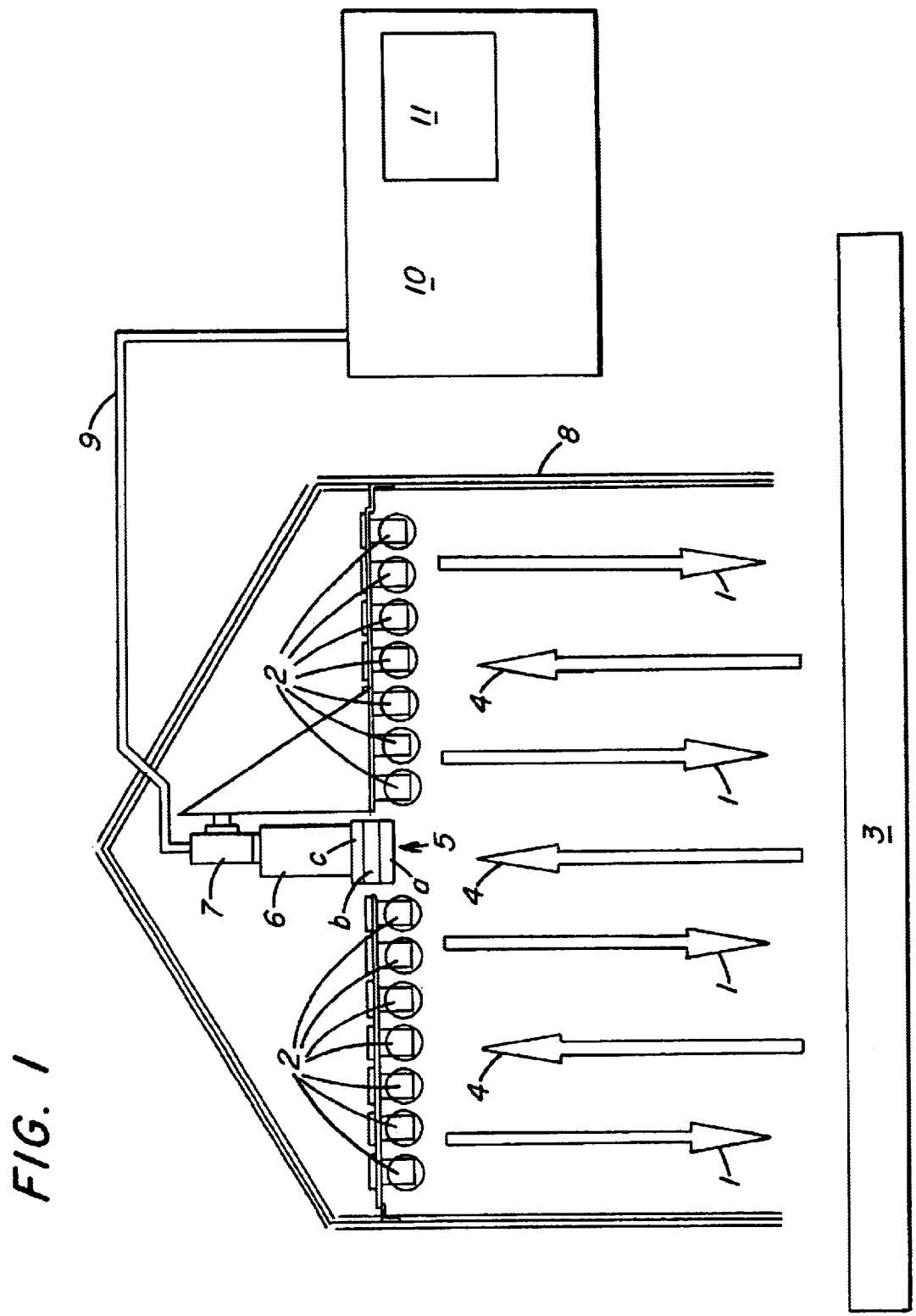
FIG. 1 is a schematic representation of an apparatus suitable for determining binder distribution by UV fluorescence in which the results are color enhanced before being displayed.

As shown in FIG. 1, long wave ultraviolet radiation 1 (i.e., electromagnetic radiation or light having wave lengths between 300 and 400 nm) emitted from lamps which emit long wave ultraviolet waves 2 is directed to the sample 3 (i.e., the composite-forming material or substrate) in a manner such that only light from the UV source, lamps 2, illuminates the sample 3 and that the flux density of UV radiation 1 is constant across the surface of sample 3. The binder molecules present in sample 3 absorb UV radiation 1 emitted by lamps 2 and fluoresce or emit visible radiation 4 (light having characteristic wavelengths between 400 and 700 nm).

Visible radiation 4 emitted by the fluorescing binder in sample 3 is passed through filter 5 and lens 6 before being imaged by video camera 7. Filter 5 as shown in FIG. 1 is a "sandwich" composed of three individual filters. The first filter 5a (i.e., the filter closest to sample 3) is a UV blocking filter. The second filter 5b (or filter next closest to sample 3) is a long pass filter having a cutoff in the blue spectrum. The third filter 5c (or filter nearest video camera 7) is a visible band-pass filter.

Video camera 7 may be a monochrome or color video camera. If a monochrome video camera is used, the wavelength of the visible band-pass filter 5c in filter 5 is chosen so that only those wavelengths specific to the binder fluorescence will pass through. In practice, a color video camera has been found to be more versatile, particularly in cases where interference from another material that may fluoresce (e.g., waxes, mold release agents, preservatives and wood rot) may be present. When a color video camera is used as camera 7, the visible band-pass filter 5c in filter 5 may be eliminated and the long-pass filter 5b can be used to block any wavelengths shorter than 435 nm. Both color and monochrome video cameras are generally equipped with an internal near infrared blocking filter (not shown). A near infrared blocking filter is necessary to eliminate any near infrared emissions of UV source 2.

In FIG. 1, filter 5 is mounted directly onto lens 6. However, it is not necessary that filter 5 and lens 6 be physically connected or attached. The relative positions of filter 5 and lens 6 may also be reversed. It is sufficient to arrange filter 5 and lens 6 so that only visible radiation 4 that has passed through filter 5 and lens 6 is imaged onto camera 7.

UV source 2, filter 5, lens 6, and camera 7 are positioned within housing 8 in the apparatus shown in FIG. 1. As shown, housing 8 is open at the bottom to allow the passage of UV radiation 1 from UV source 2 to sample 3, and visible radiation 4 from sample 3 to filter 5. Housing 8 also prevents outside light from illuminating sample 3 and or passing through filter 5. Housing 8 is a preferred but not an essential feature of the apparatus of the present invention.

The images captured by video camera 7 are relayed via video cable(s) 9 to image processing hardware 10. Image processing hardware 10 is typically a computer equipped with a high speed video frame capture board (not shown) and software capable of image analysis. When a monochrome video camera 7 is used, the image analysis software enhances the contrast between the fluorescing binder and the non-fluorescing background of sample 3, calculates the binder dosage based on the average image intensity, and displays the image as a false color image. The false color image is generated by converting the gray scale of the monochrome image to a color palette as shown in FIGS. 3–7 with the color palette used shown as a strip along the bottom of the image going from low to high left or right When a color video camera 7 is used, the image analysis software analyzes each of the red, green and blue images separately in order to discriminate the binder from any other interfering fluorescent material, calculates the binder dosage and displays the binder distribution.

The determined binder dosage and distribution levels may then be displayed on the monitor 11, printed or converted to an analog signal for output to other instrumentation. The results may be in the form of an image of the sample in the actual fluorescing color or a false color image with a pallet reflecting binder dosage.

Under actual production conditions, sample 3 would typically be on a conveyor belt that is moving at a rate of from about 5 to about 30 feet per minute. The field of view of video camera 7 may be adjusted with zoom lens 6. The field of view is generally set to cover the maximum area that is evenly illuminated by UV source lamp 2, preferably an area 2 feet long and 1.5 feet wide, directly below camera 7. At 30 feet per minute, for example, it takes about 3 seconds for the composite material 3 imaged by video camera 7 to move completely out the field of view of camera 7. This time frame is more than sufficient for the image analysis software to analyze the image for dosage and distribution of the binder and to display the results of this analysis. Continuous, real-time monitoring of a composite production process is therefore achieved with the apparatus of the present invention.

The long wave ultraviolet radiation source 2 may be any device which emits long wave ultraviolet radiation, i.e., radiation having wavelengths between 300 and 410 nanometers, preferably between 300 and 400 nanometers. Examples of suitable ultraviolet radiation sources include lamps with mercury vapor bulbs having long wave ultraviolet filters and lamps having long wave ultraviolet fluorescent bulbs such as General Electric ultraviolet bulbs such as bulbs F40T12/BLB (commercially available from GE Lighting of Cleveland, Ohio).

While it is possible to use only one ultraviolet lamp as the UV source in the apparatus of the present invention, it is preferable that more than one lamp be included in the apparatus. It is particularly preferred that from 8 to 20, most preferably about 14, lamps be included in the monitoring apparatus of the present invention to ensure even illumination of the sample surface being monitored.

Figure 10:
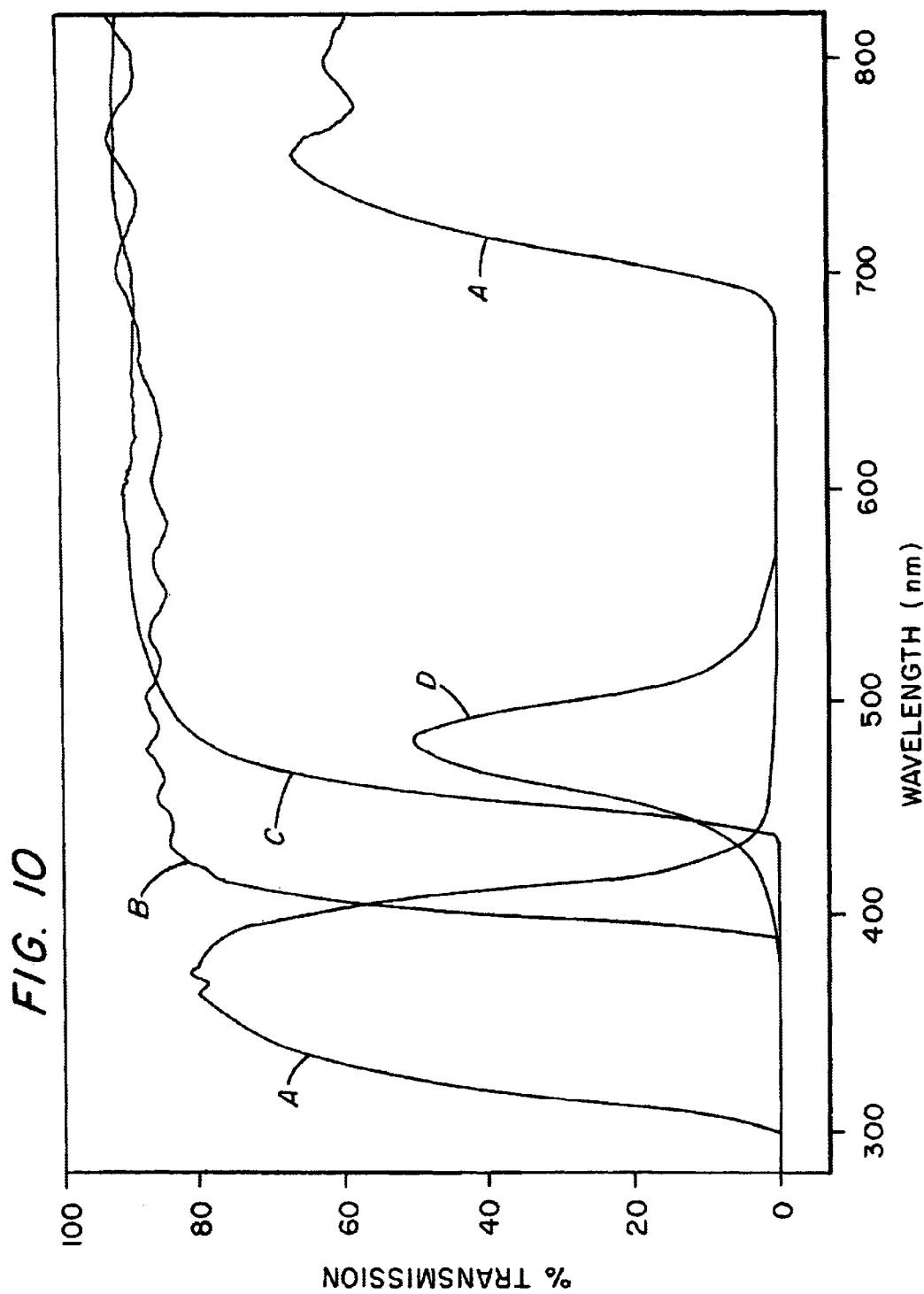
FIG. 10 is a reproduction of the transmission spectra of the filters used in the filter "sandwich" through which fluorescent waves are passed before those waves are passed through the lens and video camera.

In the embodiment of the present invention illustrated in FIG. 1, fourteen lamps with 40 watt fluorescent UV long wave bulbs each of which is 48 inches long (GE F40T12/BLB) are spaced 1.75 inches from center. The transmission spectrum of the UV filter glass of the GE F40T12/BLB bulb is shown in FIG. 10 as Curve A. The emission spectrum of the phosphorus used in the GE bulbs is centered at 360 nm. The emission spectrum of the GE UV fluorescent bulbs follows Curve A in the spectrum reproduced as FIG. 10 between 300 and 400 nm.

The composite-forming material sample 3 may be made up of any of the materials, particularly lignocellulosic materials, known to be useful for the production of composite materials to which a binder, preferably an isocyanate-based binder, has been applied. Examples of suitable composite-forming materials include: wood, wood fibers, wood bark, cork, bagasse straw, flax, bamboo, esparto, rice husks, sisal fibers and coconut fibers. Wood strands, shavings and chips used in the production of engineered lumber known as oriented strand board ("OSB") are particularly preferred. The strands, chips or shavings may vary in size from 0.03"×0.18"×2.0" to 0.12"×2.0"×28.0'. The preferred size ranges from 0.03"×1.0"×16" to 0.12"×2.0"×24" and the most preferred range is from 0.03"×0.75"×3.0" to 0.12"×2.0"×24". These lignocellulosic materials may have a moisture content of from about 0.5 to about 30% by weight, based on total weight of material, preferably from about 3 to about 8% by weight when used in the production of a composite material.

Any of the binder compositions having a fluorescing component that are known to be useful for the production of composite articles may be used to produce composite articles in accordance with the present invention. Such known binders include isocyanates. The preferred binder compositions are polyphenylene polymethylene polyisocyanates which contain higher molecular weight oligomers (i.e., oligomers having more than four rings) that have an inherent fluorescence and thus do not require the addition of a fluorescing agent to the binder composition. The binder should have a minimum of 35% by weight of oligomers with more then four rings.

Figure 2A:
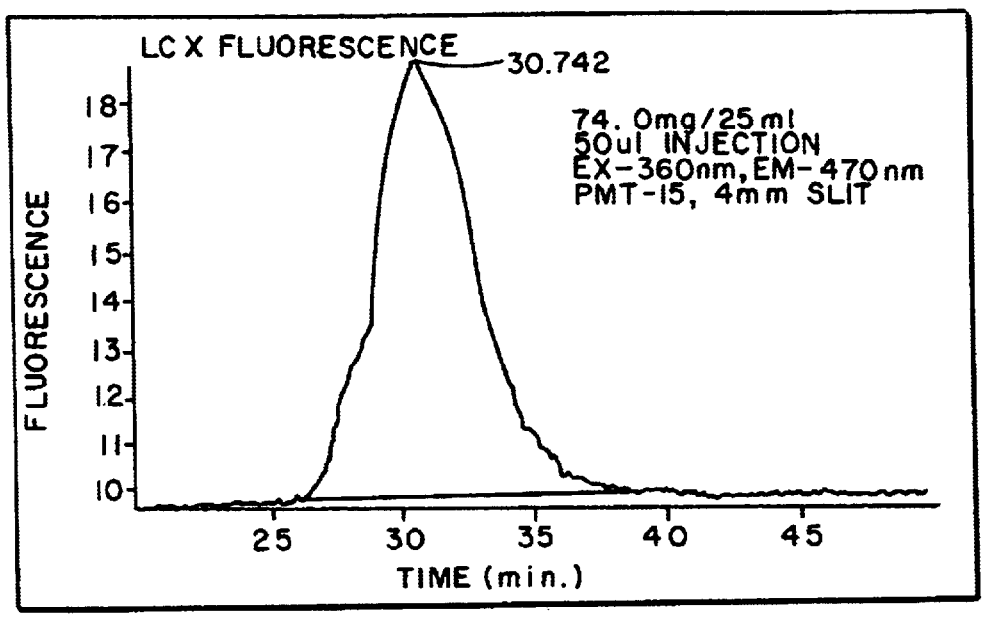
FIG. 2 is a reproduction of chromatographic analyses of the polymeric MDI (i.e., polyphenyl polymethylene polyisocyanate) in the binder composition used to coat the wood strand images shown in FIGS. 3–7. These chromatographs were generated using a Hewlett Packard size exclusion chromatograph having dual UV-absorption and UV-fluorescence detectors.
Figure 2B:
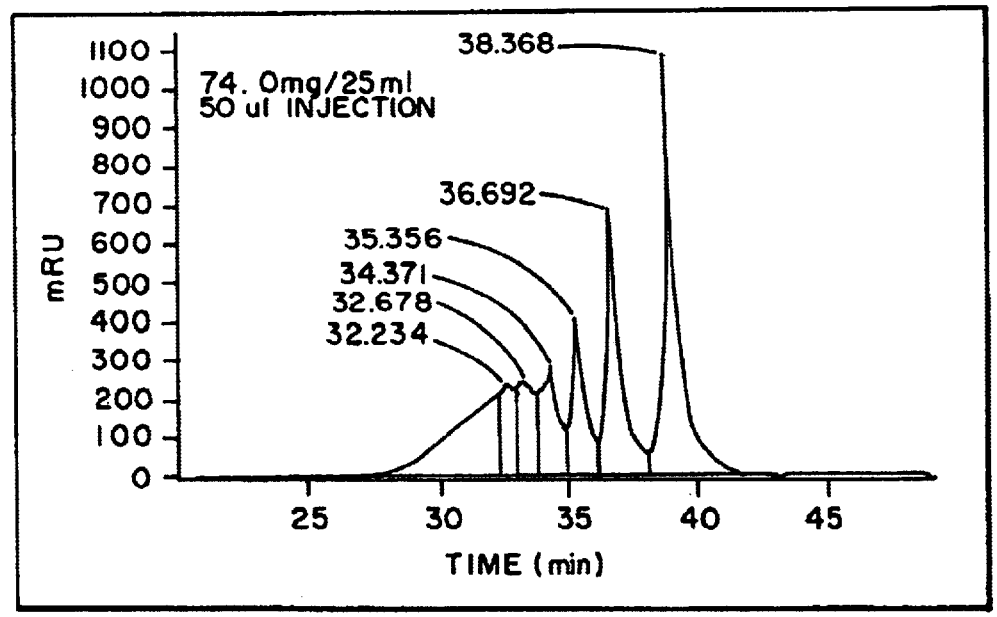

FIGS. 2A and 2B are reproductions of the chromatographic analyses of the polymeric MDI used in the Examples. These chromatographs were generated using a Hewlett Packard size exclusion chromatograph (Model 1090M) with dual UV absorption and UV fluorescence detectors. The UV fluorescence peak in FIG. 2A that eluted between 26 and 36 minutes (maximum at 30.8 minutes) is associated with the highest molecular weight oligomers of FIG. 2B eluting out on the UV absorption detector. The UV fluorescence peak essentially disappears upon the appearance of the 4-ring, 3-ring and monomer peaks at 35.4, 36.7 and 39.0 minutes respectively in FIG. 2B. Monitoring isocyanate binder fluorescence thus appears to be a viable method for monitoring a commercial wood composite production process.

Ideally, the binder would be used in an amount sufficient to coat 100% of the surface area of the material to be bonded. If even distribution of the binder is achieved, the amount of binder necessary to achieve approximately 100% coverage is minimized. However, in commercial production processes, the binder dosage may be as much as 50 to 60% greater than the amount theoretically necessary to achieve 100% coverage in order to ensure complete coverage.

Filter 5 shown in FIG. 1 is a multi-layer "sandwich" arrangement of filters. The first layer 5a (nearest to sample 3) is a UV blocking filter that protects the other filters and video camera CCD (Charge Coupled Device) imaging detector from UV damage. Any commercially available UV blocking filter that blocks UV radiation wavelengths shorter than 380 to 400 nm (preferably shorter than 400 nm) may be used as the blocking filter 5a. Examples of suitable blocking filters include filters made with the polycarbonate plastic having a UV stabilizer that are commercially available under the names Makrolon (Bayer Corporation) and Lexan (GE Plastics). A 0.125 inch thick sheet of Makrolon plastic filter is particularly preferred. Curve B in FIG. 10 is a transmission spectrum of optical grade polycarbonate with the UV blocking cutoff at 400 nm.

The second filter layer 5b of filter 5 is a long-pass filter that blocks the UV and short wavelength blue between 400 and 455 nm (preferably all wavelengths shorter than 455 nm). Any of the commercially available long-pass filters with a sharp cutoff at 455 nm may be used as filter 5b in filter 5. The 455 nm long-pass filter F45,063 which is commercially available from Edmund Scientific, Barrington, N.J.) is particularly preferred. Curve C in FIG. 10 is a transmission spectrum of the Edmund Scientific 455 nm long-pass filter F45,063.

The third filter layer 5c of filter 5 is a visible band-pass filter selected to increase the contrast between the binder and the composite material and eliminate any interference from other fluorescing components. For example, if the binder composition is based on polymeric MDI and camera 7 is a monochrome video camera, the preferred visible band-pass filter 5c of filter 5 is a blue filter. Any of the commercially available blue band-pass filters with a band-pass between 400 and 530 nm would be suitable. A visible band-pass filter that has been found to be particularly useful in the apparatus of the present invention is Edmund Scientific's Night Blue transparent acrylic filter from filter assortment F39418. Curve D in FIG. 10 is a transmission spectrum of this Night Blue transparent acrylic filter.

Filter 5 need not be a sandwich structure. It is possible to have a custom optical interference filter made that would have all of the characteristics of filter 5a, 5b, and 5c. However the cost would be considerably higher unless a large number of filters were made at one time. The illustrated filter sandwich cost less than $100. A custom interference filter may cost in excess of $500.

Any of the commercially available lenses may be used in the practice of the present invention. The lens does not have to be a zoom lens, however, a zoom lens makes it easy to adjust the field of view to cover the maximum area that is evenly illuminated by the UV source 2. A particularly preferred lens 6 is Edmund Scientific's 8 to 48 mm zoom lens F53152.

Any of the commercially available video cameras may be used in the practice of the present invention as video camera 7. This camera may be either a monochrome or a color camera. Examples of suitable video cameras include the Sony Model XC-75 monochrome camera and Cohu Model 2222-2340 color camera. Each of these cameras is available from Edmund Scientific, Barrington, N.J.

Filter 5, lens 6 and camera 7 are positioned with respect to sample 3 in a manner such that the field of view of camera 7 is adjustable with lens 6. Video camera 7 is set to cover the maximum area that is evenly illuminated by UV source 2. It is preferred that there be a distance of about 48 inches between the surface of sample 3 and lens 6 and that the field of view be an area of about 2 feet in length and about 1.5 feet in width directly below camera 7. Filter 5, lens 6 and camera 7 are positioned with respect to each other in a manner such that all light falling on the CCD (Charge Coupled Device) image detector of camera 7 will have passed through filter 5 and lens 6.

Housing 8 is a supporting structure that is helpful for maintaining the alignment of UV source 2, filter 5, lens 6 and camera 7 and shielding the composite-forming material 3 in the field of view of camera 7 from external light. Housing 8 will usually be open at its bottom to allow passage of UV radiation from UV source 2 to the composite-forming material 3 and to allow passage of the fluorescent light back to filter 5, lens 6 and camera 7.

Any of the commercially available computers with a high-speed video frame capture board may be used as image processing hardware 10 in the apparatus of the present invention. Computers which have been found to be particularly advantageous are those having a 233 MHz or faster Intel Pentium Processor with video frame capture board such at that which is available under the name "Bandit" from Coreco, Inc., Quebec, Canada.

Any of the commercially available image processing software programs that can be installed on computer hardware 10 may be used in the apparatus of the present invention. One software program that has been found to be particularly advantageous in the practice of the present invention is the Wit Visual Programming Software that is available from Logical Vision, Quebec, Canada.

Any of the commercially available monitors may be used in the practice of the present invention as monitor 11. It is preferred, however, that any monitor employed be capable of displaying images and/or spectra in color.

The material to be monitored in accordance with the present invention (i.e., the substrate) is generally prepared by mixing or blending a lignocellulose-based material with the binder, depositing the composite-forming mixture or blend into a mold or a form of some sort on a conveyor belt, passing that composite-forming material under housing 8 to monitor dosage and distribution of the binder, and passing that composite-forming material through a heated press to cure the binder composition. The press is typically maintained at a temperature of from about 50 to about 210° C., preferably from about 150 to about 200° C. to ensure cure of the binder.

Figure 6:
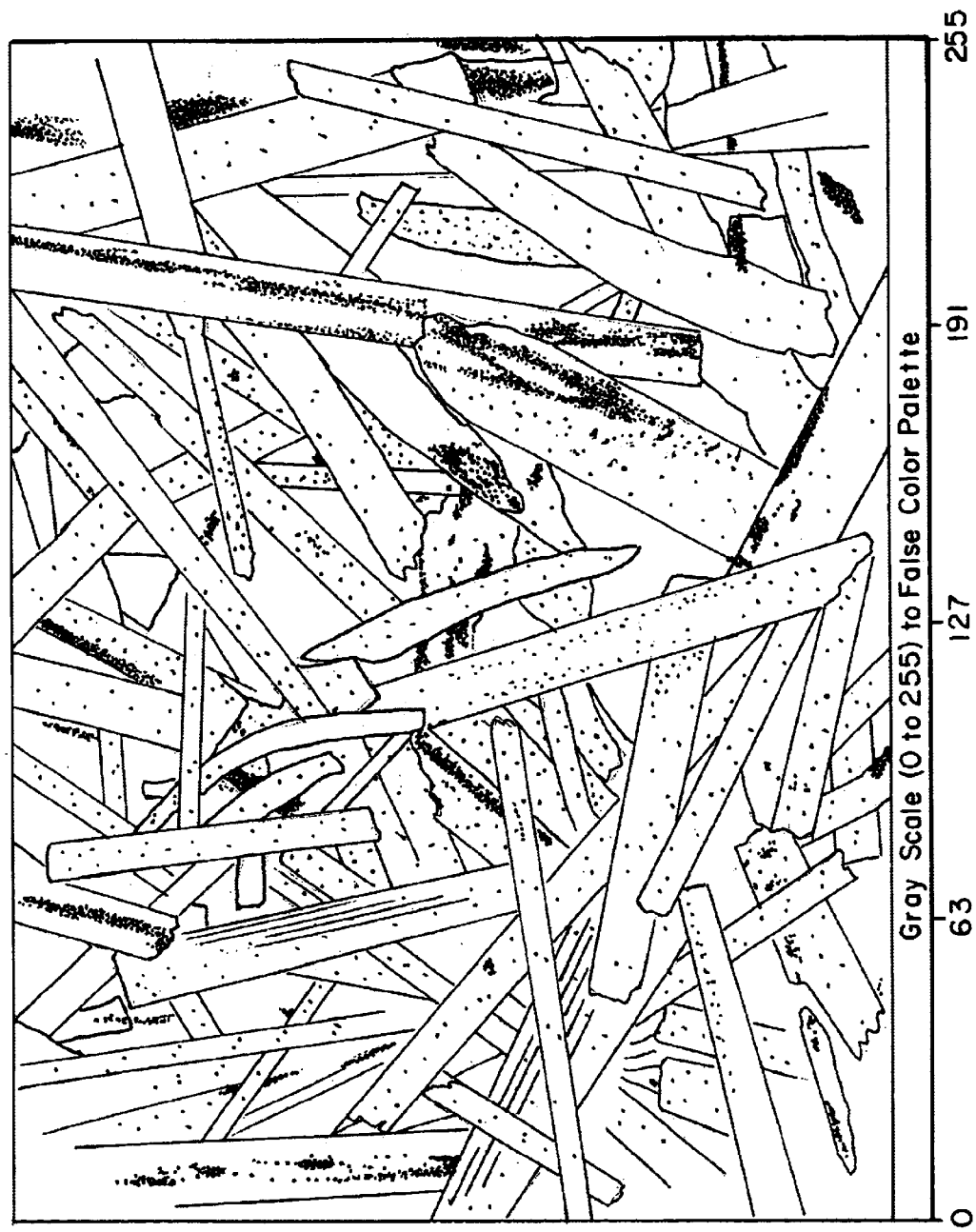
FIG. 6 is a false color representation of the UV fluorescent image of wood strands coated with 6% polymeric MDI.
Figure 7:
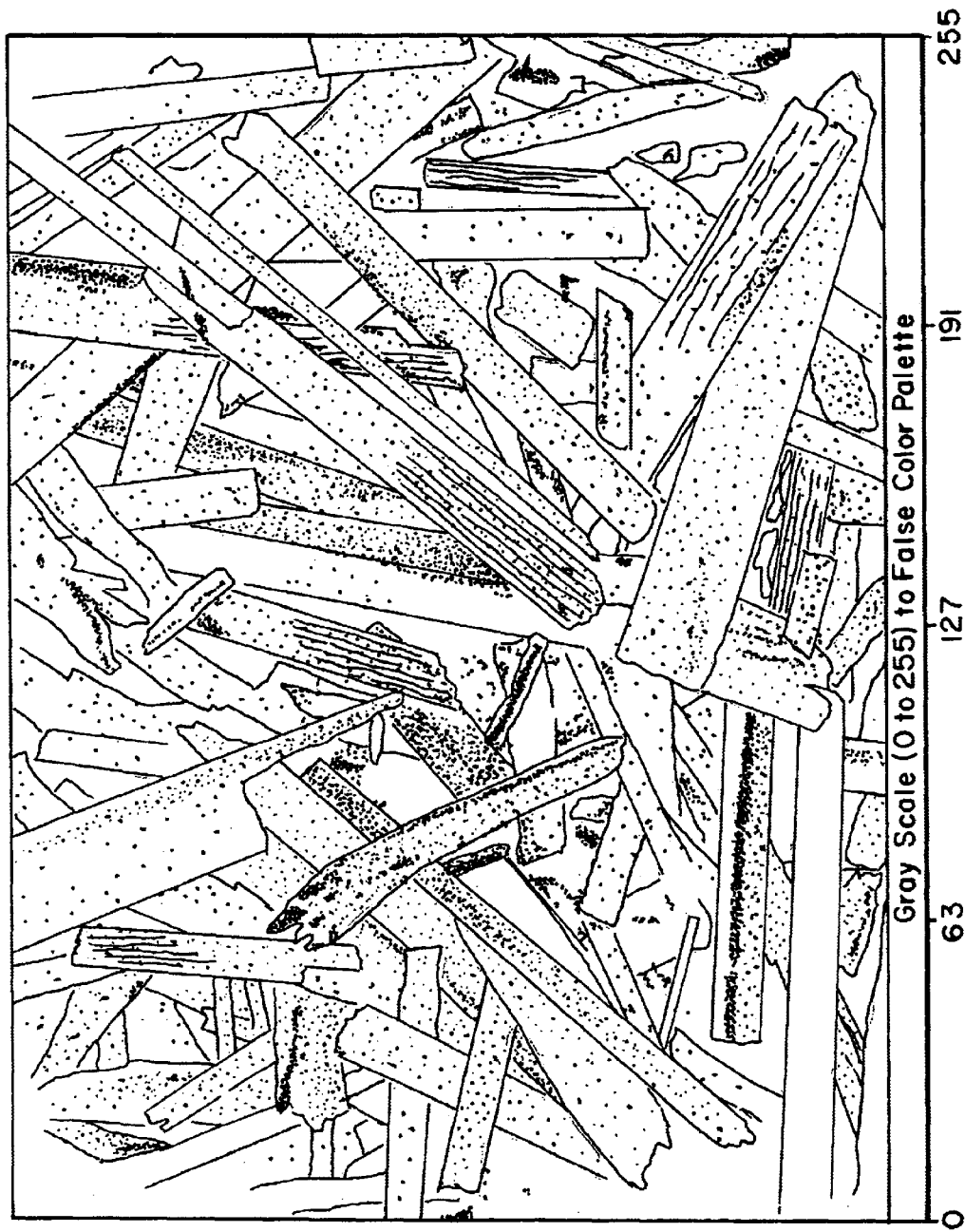
FIG. 7 is a false color representation of the UV fluorescent image of wood strands coated with 8% polymeric MDI.

FIGS. 3–7 show the UV fluorescence images of wood strands that have been coated with polymeric MDI at levels of 0%, 2%, 4%, 6%, and 8% by weight binder, based on the weight of the wood strands, using a 6 foot diameter lab blender (available from Coil Industries, Vancouver, Canada). The images in these FIGS. 3–7 are false color representations of the monochrome gray scale. Wood rot fluoresces very brightly and appears red and red orange in color. Wood strands with no binder are dark blue in color and strands coated with binder appear light blue to green to yellow in color as the binder dosage increases. Examination of the central two-thirds of the images where the CCD (Charge Coupled Device) image detector illumination is constant, shows that there is a very uneven distribution of binder on the strands. If the binder shown in FIG. 5 at 4% dosage had been distributed evenly over all of the strands, 4% dosage would be sufficient to produce the composite article. FIG. 6 shows that even at a 6% dosage level some strands are not adequately coated. FIG. 7 shows that at 8% dosage all strands are covered with binder but many strands are over-dosed and the excess binder is wasted. The ability to monitor binder dosage and distribution achieved with the apparatus of the present invention will make it possible to optimize the production process and achieve significant savings due to the use of less binder.

Having thus described our invention, the following Examples are given as being illustrative thereof. All parts and percentages given in these Examples are parts by weight and percentages by weight, unless otherwise indicated.

EXAMPLES

Example 1

An apparatus corresponding substantially to that shown in FIG. 1 was used to analyze long strands of aspen wood to which polymeric MDI (Mondur 541 which is commercially available from Bayer Corporation) was applied at levels of 0%, 2%, 4%, 6% and 8% to calibrate the device for dosage.

The UV source 2 was made up of eight lamps having 4 foot 40 watt bulbs (F40T12/BLB bulbs available from GE Lighting, Cleveland, Ohio), and four lamps having 2 foot 20 watt bulbs (F20T12/BLB bulbs available from GE Lighting, Cleveland, Ohio). The lamps were arranged symmetrically around filter 5, lens 6 and video camera 7 as shown in FIG. 1 to evenly illuminate the aspen strands which were 48 inches from the UV lamps 2.

Composite-forming material 3 was composed of aspen wood strands ranging in size from 0.08"×1.0"×6" to 0.12"×1.5"×12" and having a moisture content of 6% by weight. 0%, 2%, 4%, 6% or 8% by weight of polymeric MDI which is commercially available from Bayer Corporation under the name Mondur 541 was applied to these strands.

Filter 5 was a filter sandwich made up of two layers. The first layer was a polycarbonate UV blocking filter made up of 0.125" thick Makrolon polycarbonate with UV stabilizers (commercially available from Shefsield Plastics, Shefsield, Me). The second filter layer was composed of the 455 nm long-pass filter F45,063 (available from Edmund Scientific, Barrington, N.J.).

Lens 6 was the lens F39,087 (available from Edmund Scientific, Barrington, N.J.) having f/1.3–16 and 8.5 mm focal length.

Video camera 7 was a Sony model XC-75 monochrome camera (available from Edmund Scientific). A 75-ohm coaxial cable 9 connected video camera 7 to image processing hardware 10.

Image processing hardware 10 was a 233 MHz Pentium processor based computer with 128 Megs of RAM. The computer was a model DELL Optiple:GXA sold by Dell Computer Corporation. Bandit Video Frame Capture Board sold by Coreco Inc, Quebec, Canada was used to digitize the video signal from camera 7.

The image processing software algorithms were programmed using the Wit Visual Programming Software (available from Logical Vision, Quebec, Canada).

The aspen wood strands were dosed with polymeric MDI in a six foot diameter lab blender (Coil Industries, Vancouver, Canada). The strands were dosed with binder in 2% increments and then passed under the monitoring apparatus of the present invention. The aspen wood strands were covered with a cardboard shield to prevent exposure to the UV radiation until the image processing software was ready to capture the video image. Exposure to UV radiation for periods of longer than 15 to 30 seconds will bleach the composite material and reduce the overall fluorescence enough to affect the calibration. Actual exposure to the UV radiation to capture an image takes only 0.1 second. After the image was captured, the wood strands were placed back in the blender to be dosed with another 2% of binder. This process was repeated until images at 0%, 2%, 4%, 6% and 8% binder were obtained.

Figure 3:
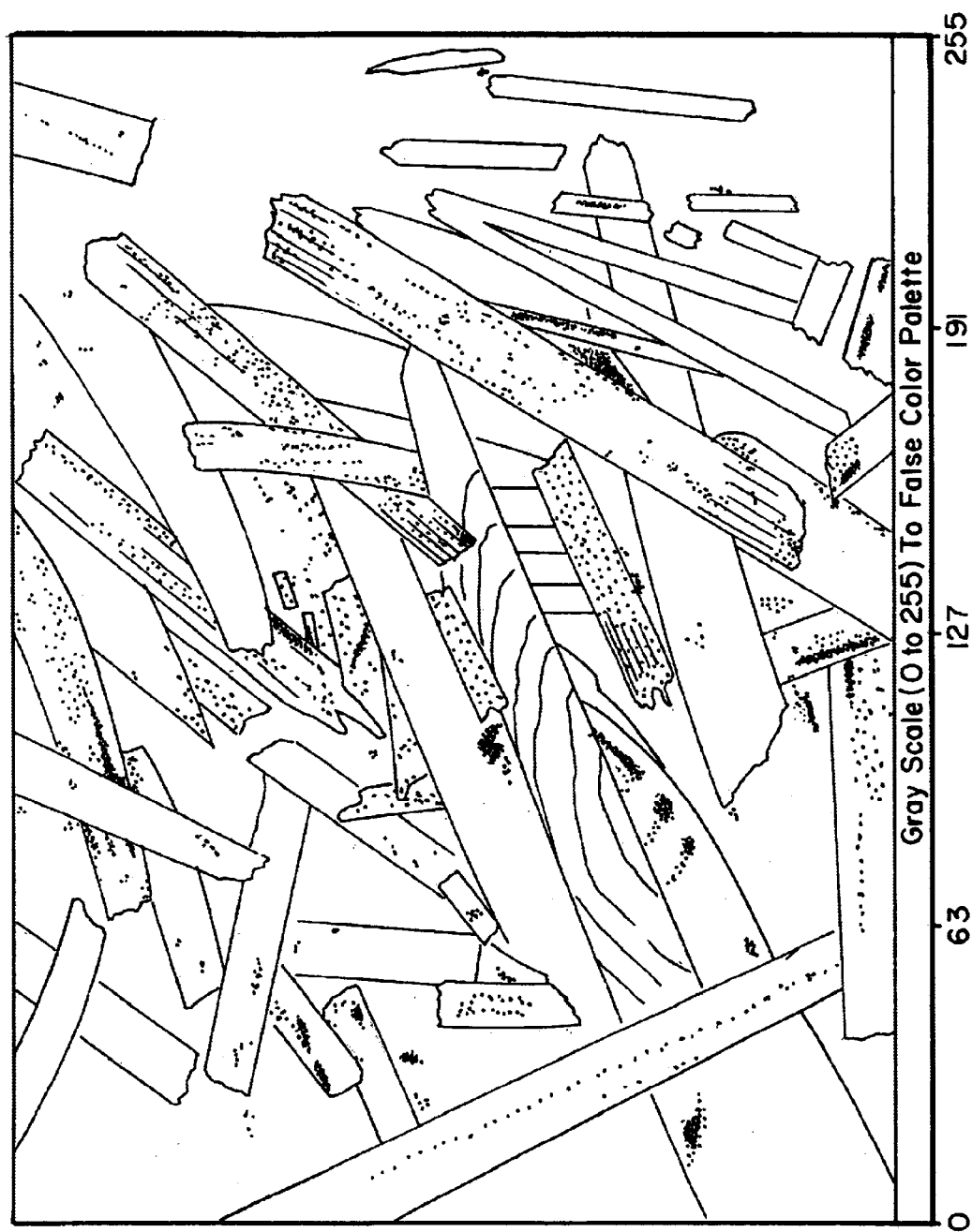
FIG. 3 is a false color representation of the UV fluorescent image of wood strands coated with 0% polymeric MDI.
Figure 4:
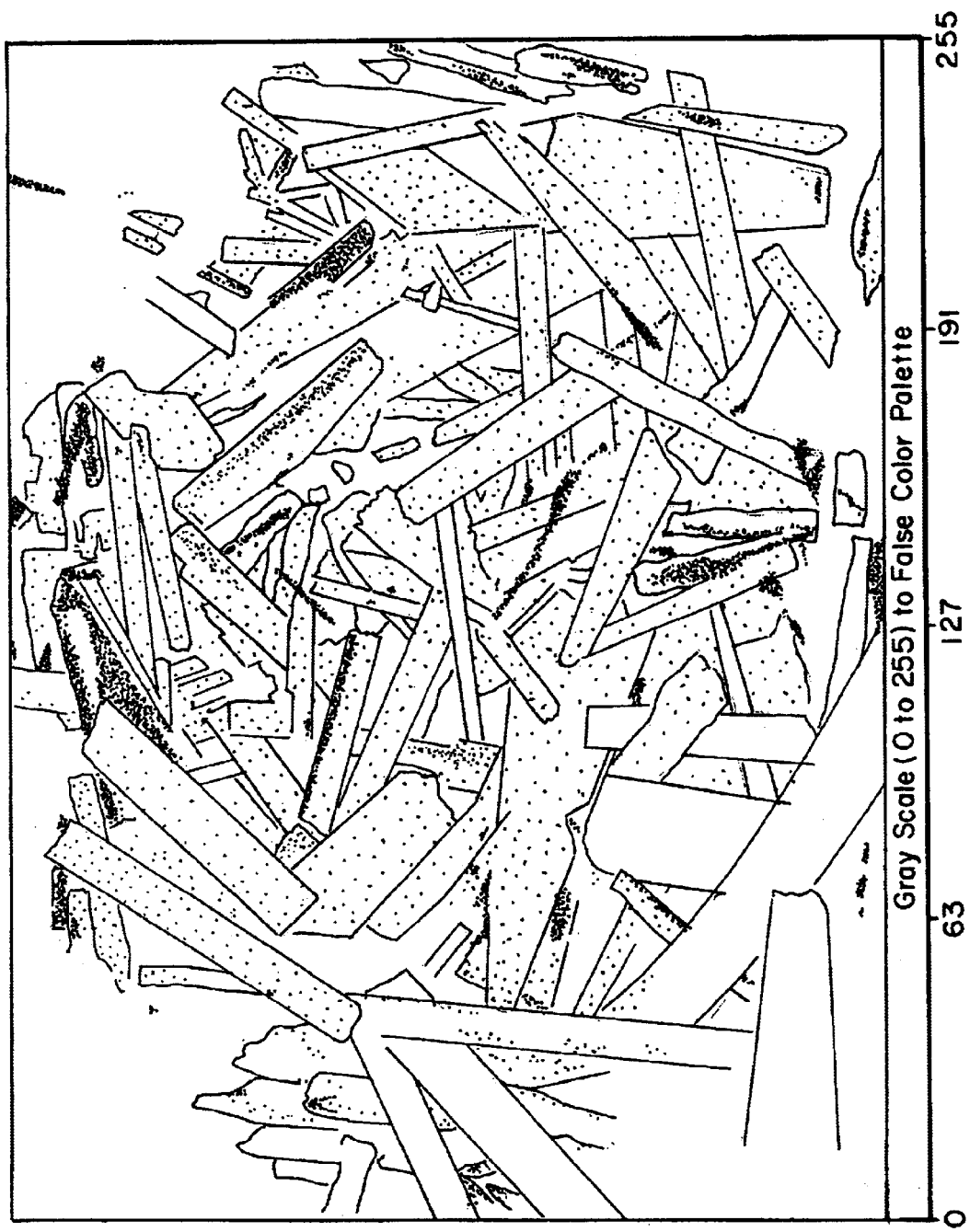
FIG. 4 is a false color representation of the UV fluorescent image of wood strands coated with 2% polymeric MDI.
Figure 5:
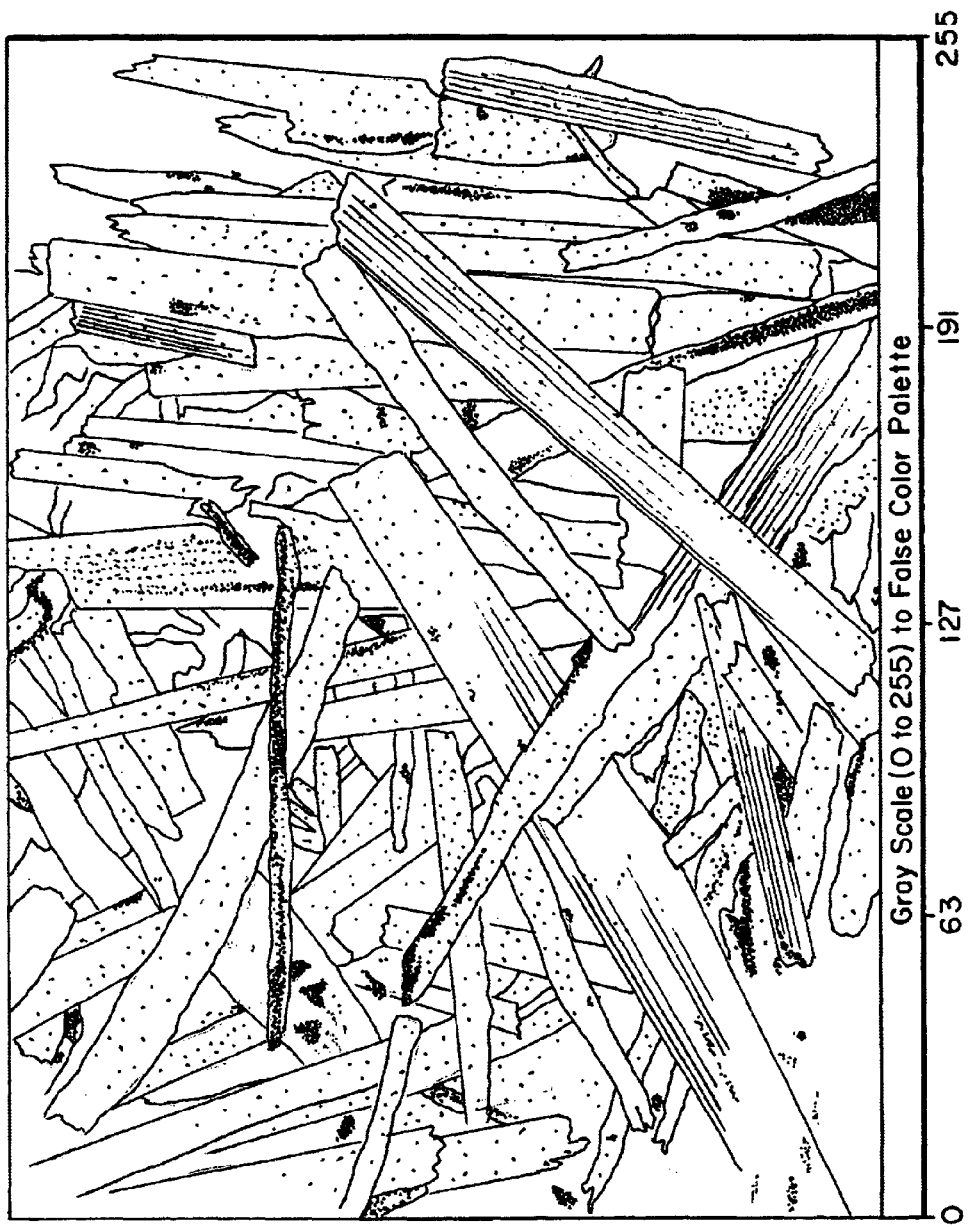
FIG. 5 is a false color representation of the UV fluorescent image of wood strands coated with 4% polymeric MDI.

The monochrome images were then processed using the Wit software by adjusting the contrast equally on each image and converting to a false color pallet to represent the gray scale. The false color images are shown in FIGS. 3–7. Because the filters used will allow all visible light having wavelengths between 455–700 nm, there is no discrimination between the binder and the other fluorescing materials such as wood rot. However, the intensity of the yellow fluorescence of the wood rot is considerably greater than the blue green fluorescence of the polymeric MDI binder. When the monochrome images are converted to false color, the high intensity wood rot is shown as orange and red and the binder is shown as light blue to green to yellow depending upon the binder dosage. The 0% resin image of FIG. 3 shows some light blue in the center of the image which is the result of the weak natural deep blue fluorescence of the wood under long wave UV and higher light throughput in the center of the image, a characteristic of the f/1.3–16, 8.5 mm focal length lens used as lens 6.

The image processing software was then used to calculate the histogram for each of the images. A histogram is a mathematical representation of the image in which a vector is generated by assigning a vector element for each of the 256 brightness levels of the gray scale. The value of each vector element is the total number of pixels in the image at that intensity.

Figure 8:
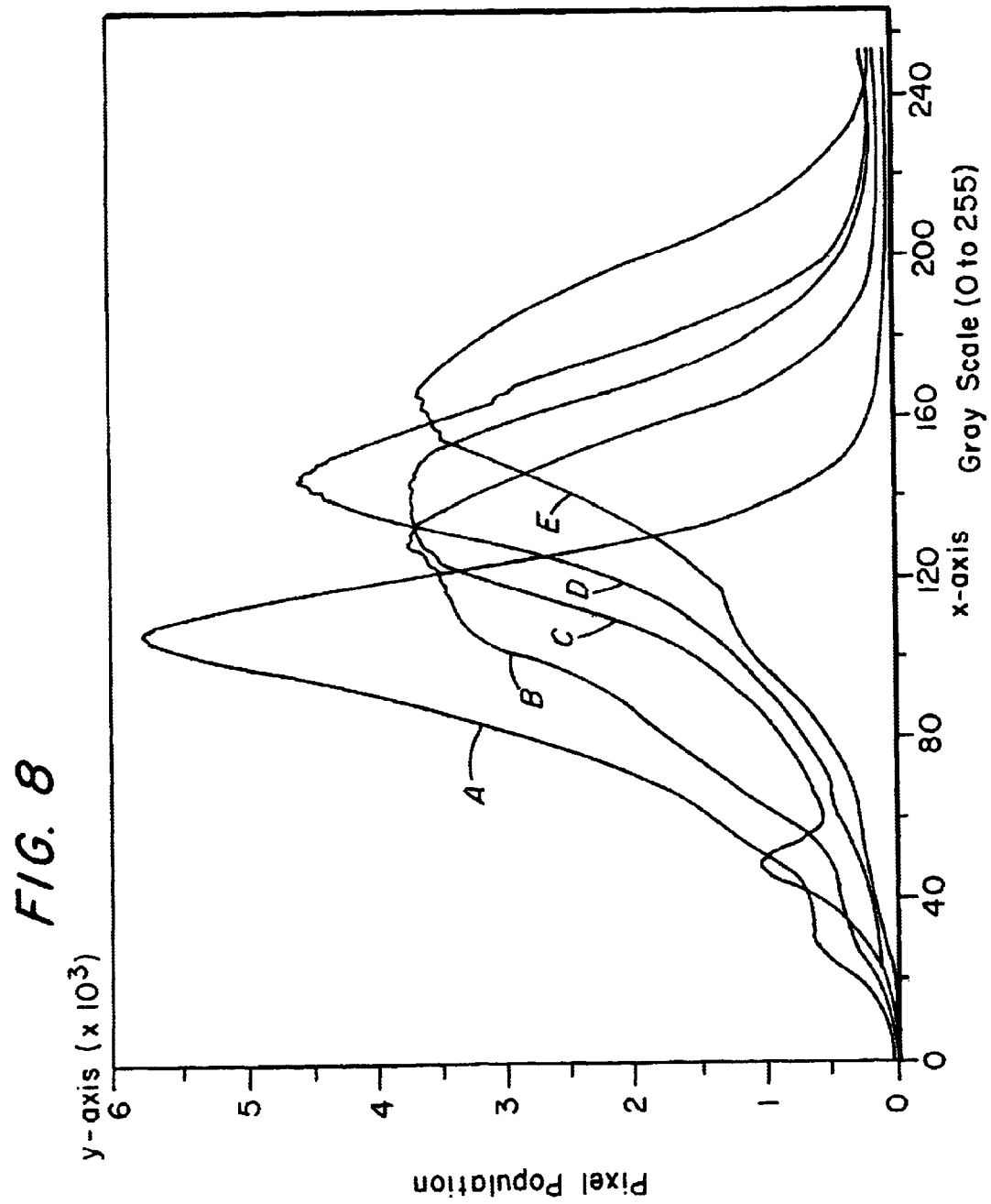
FIG. 8 is a set of histograms of the monochrome images used to generate the false color images in FIGS. 3–7 in which the number of image elements or pixel population at each level of brightness for the gray scale between 0 and 255 is plotted along the Y axis with the brightness or gray scale level plotted along the X axis.

FIG. 8 is a graphical representation of the histograms generated from the images in FIGS. 3–7. In FIG. 8, the brightness or gray level between 0 and 255 arbitrary unites is plotted on the x-axis. The number of pixels or pixel population is plotted on the y-axis. Curve A in FIG. 8 represents the histogram for the wood strands dosed with 0% binder. Curve B in FIG. 8 represents the histogram of the wood strands dosed with 2% binder. Curve C in FIG. 8 represents the histogram of the wood strands dosed with 4% binder. Curve D in FIG. 8 represents the histogram of the wood strands dosed with 6% binder. Curve E in FIG. 8 represents the histogram of the wood strands dosed with 8% binder. The wood rot shows up as the positive step in the histograms at the upper end of the x-axis.

Figure 9:
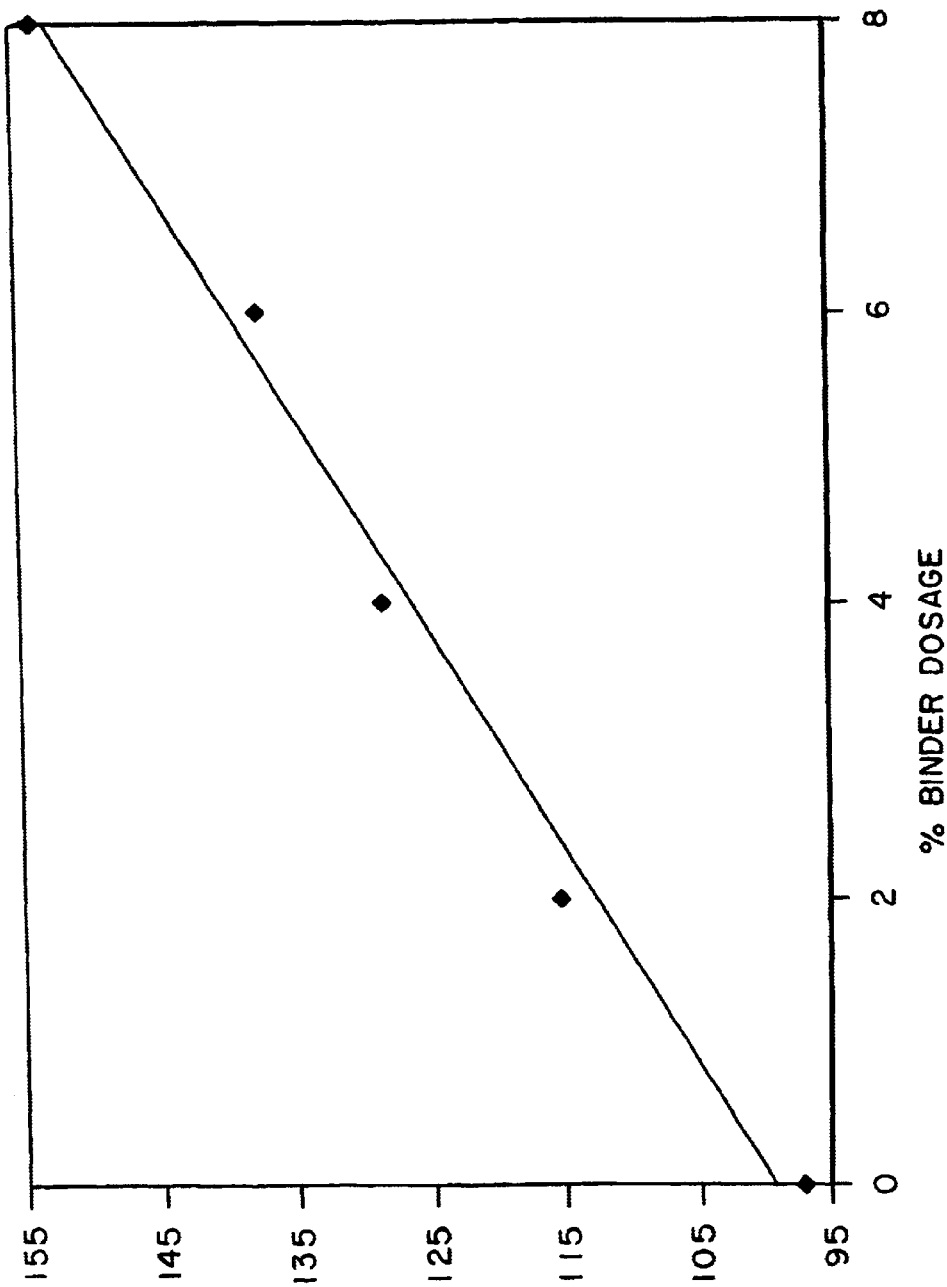
FIG. 9 is a linear regression of the predicted binder dosage based on average brightness of the monochrome images used to generate the false color images in FIGS. 3–7 to actual binder dosage.

The average image intensity was calculated from the histograms by taking the cross product sum of the vector (i.e., the sum of each vector element value times that vector element's number [a number from 0 to 255]) and dividing by the total number of pixels. This calculation of average image intensity is different from the calculation for the area under the curve of the histogram. The area under the curve of the histogram would always be equal to the number of pixels (i.e., 307,200 for a 640×480 pixel image). The cross product sum weights each element of the vector with the intensity of that element. The average image intensity can then be correlated with the binder dosage using linear regression. The results of such linear regression are shown in FIG. 9.

Example 2

The apparatus used in Example 1 was modified to eliminate the interference of wood rot fluorescence when a monochrome camera is employed.

The number of lamps used as the UV source was increased. A total of fourteen lamps having 4 foot 40 watt F40T12/BLB bulbs (GE Lighting, Cleveland, Ohio) were used as UV source 2. A third layer was added to filter sandwich 5. This layer was a visible band-pass filter selected to increase the contrast between the binder and the lignocellulose material and to eliminate any interference from the fluorescing wood rot. The filter used was Edmund Scientific's Night Blue transparent acrylic filter from filter assortment F39418. Curve D in FIG. 10 is a transmission spectrum of the Night Blue filter. Lens 6 was replaced with an 8 to 48 mm zoom lens (lens F53152 available from Edmund Scientific, Barrington, N.J.).

Figure 11:
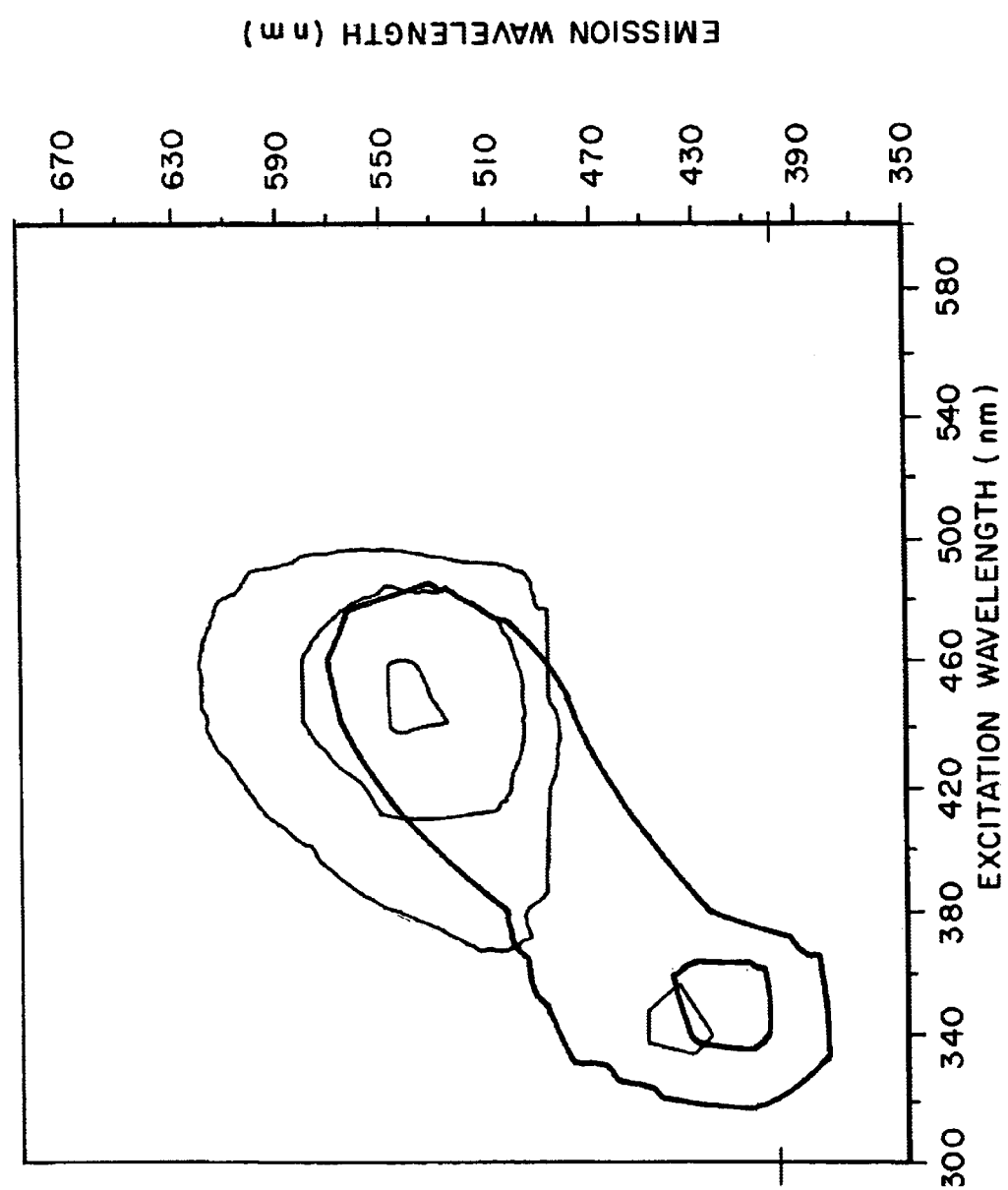
FIG. 11 is a 2-dimensional contour map of the UV fluorescence of the polymeric MDI wood binder and wood rot.

FIG. 11 is a 2-dimensional contour map of the UV-fluorescence of the polymeric MDI (Mondur 541 available from Bayer Corporation) and a yellow fluorescing wood rot extract made by soaking wood rot in tetrahydrofuran solvent for 6 hours. This UV contour map was generated using an Hitachi Model F4500 Fluorescence Spectrophotometer UV fluorescence spectrometer. In FIG. 11, the binder fluorescence is seen as the thick line contours and the wood rot fluorescence is seen as the thin line contours. The x-axis is the excitation wavelength, and the y-axis is the emission wavelength. The UV source lamps 2 have an emission spectrum following that of the lamp UV glass filter transmission spectrum shown as Curve A in FIG. 10 between 300 and 400 nm.

Given the emission spectrum of the UV source lamps 2 (Curve A in FIG. 10), the transmission spectrum of the 455 nm long-pass filter (Curve C in FIG. 10), and the Night Blue transparent acrylic filter spectrum (Curve D in FIG. 10), it can be seen from FIG. 11 that the majority of the wood rot fluorescence could be eliminated from the camera image.

Figure 12:
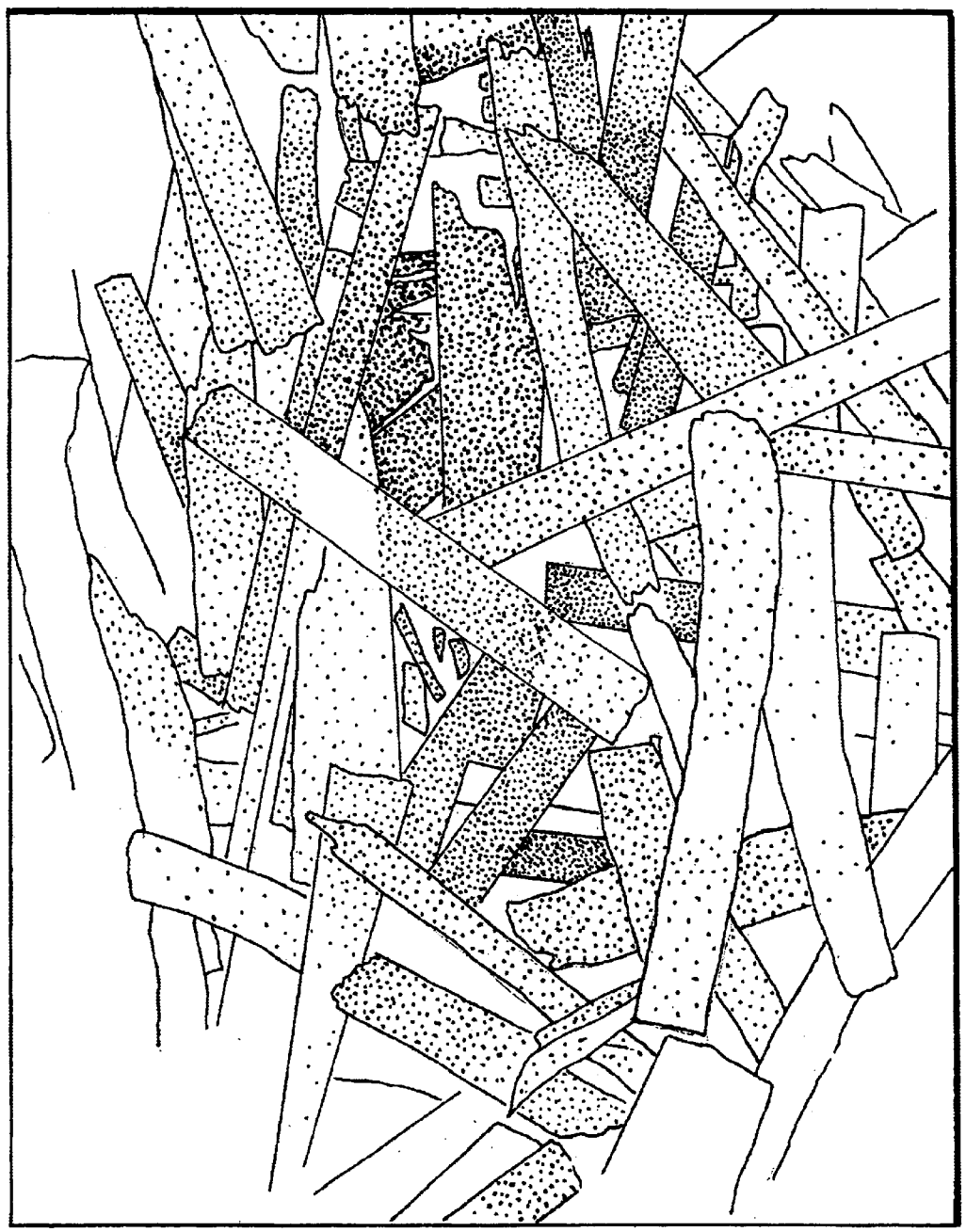
FIG. 12 is a monochrome representation of the UV fluorescent image of wood strands coated with 5% of polymeric MDI generated by using a blue band pass filter to eliminate wood rot fluorescence in the image.

Images were taken of wood strands dosed with 5% binder using the above-described modified apparatus. FIG. 12 is a monochrome image taken with this modified apparatus. It is evident from FIG. 12 that the fluorescence of the wood rot was eliminated from the image when compared to the true color image of FIG. 13. FIG. 12 shows the uneven distribution of binder over the wood strands. A vertical strand in the center of the image was partially masked by other strands in the binder dosing process.

Example 3

The apparatus used in Example 2 was further modified to allow the quantitative and qualitative analysis of multiple fluorescing materials in the composite-forming material. This was accomplished by eliminating the third layer of the filter sandwich (filter 5c), i.e., the Night Blue transparent acrylic visible band-pass filter. A Cohu Model 2222-2340 color camera (available from Edmund Scientific) was substituted for the camera used in Example 2.

Figure 13:
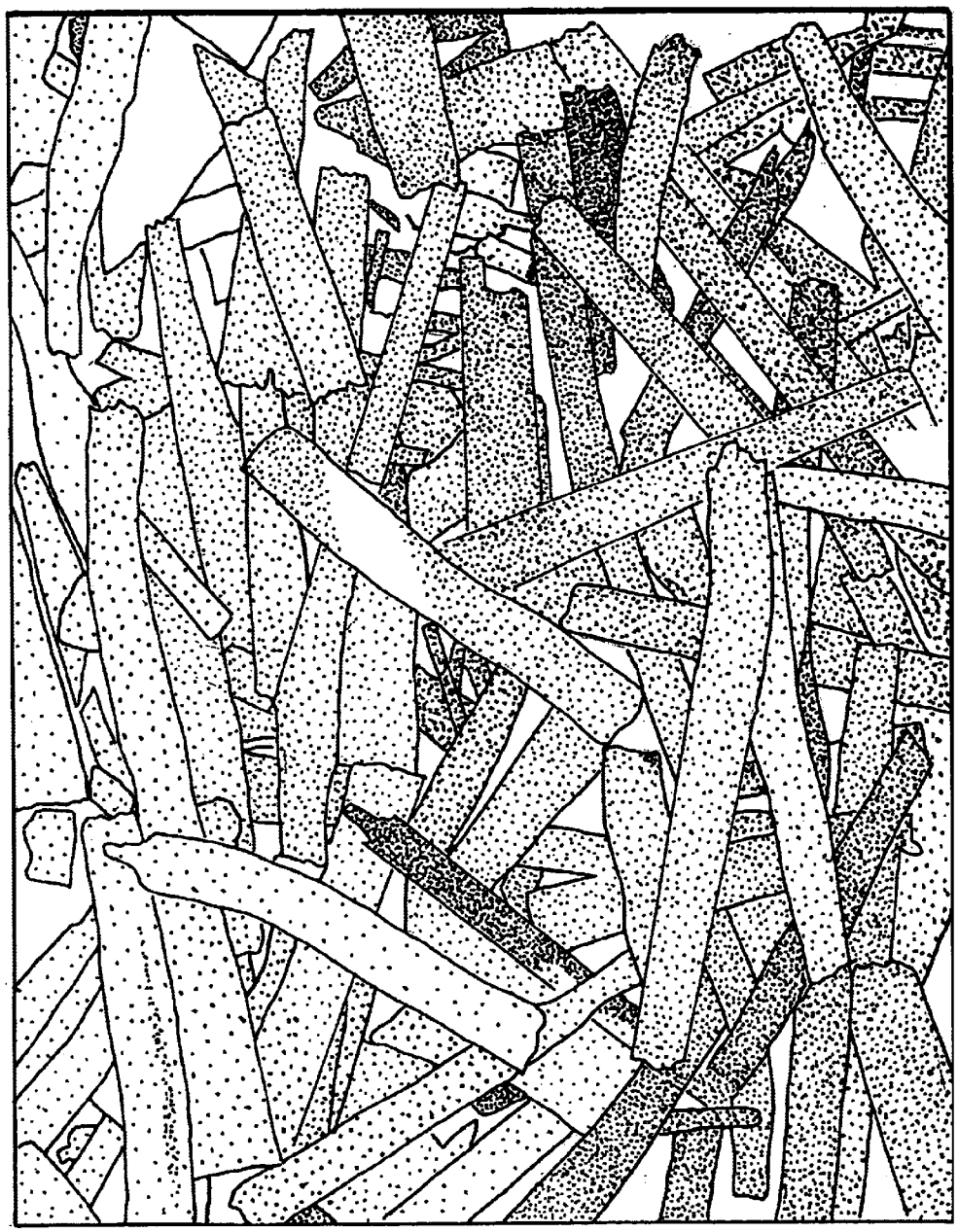
FIG. 13 is a true color image of wood strands coated with 5% polymeric MDI obtained using a color camera.
Figure 14:
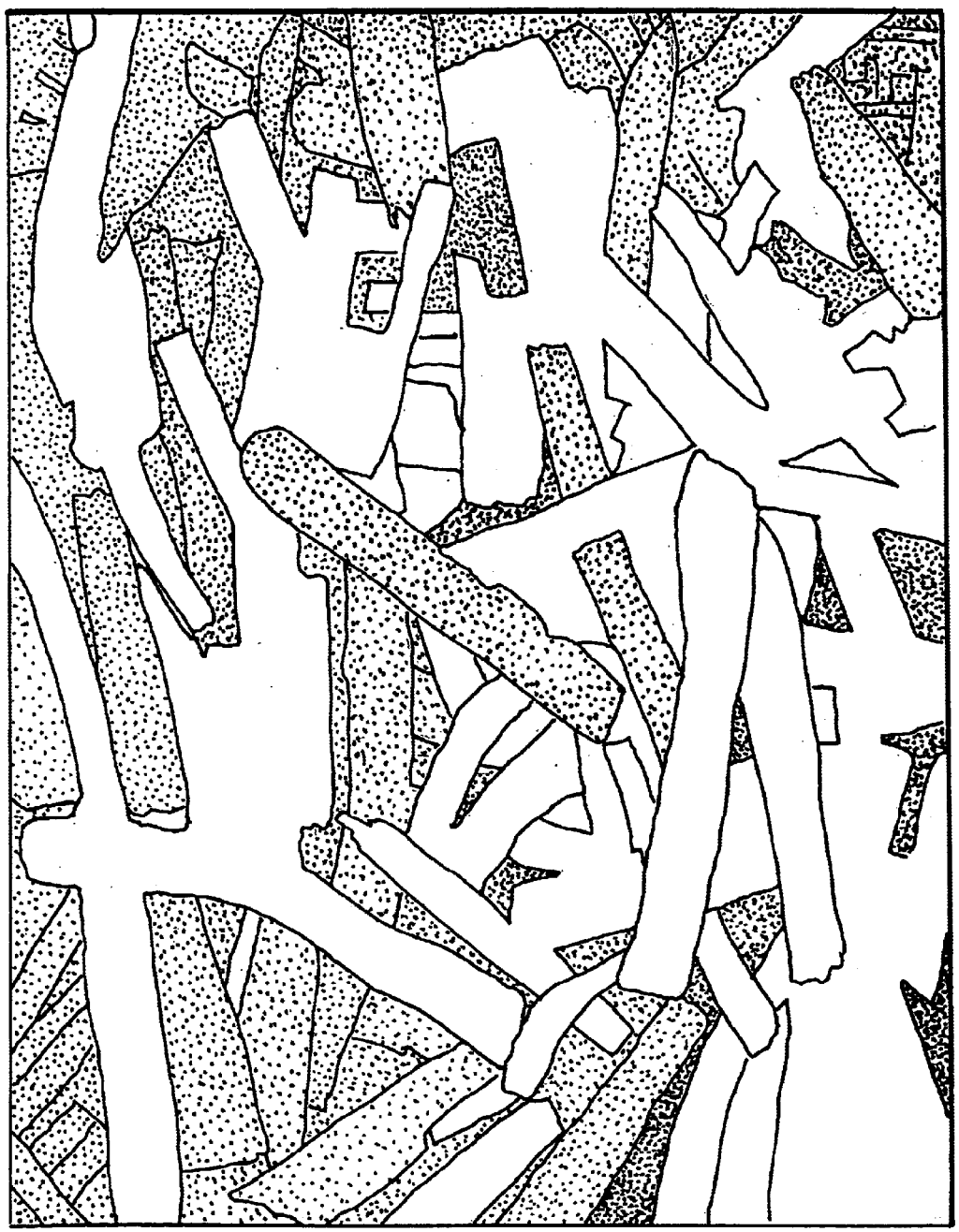
FIG. 14 is the image of FIG. 13 in which the wood rot is masked out.

Images of wood strands dosed with 5% polymeric MDI were then taken with this modified apparatus. FIG. 13 is a full color image from camera 7 in which wood rot is represented by the yellow green fluorescence, the isocyanate binder is represented by the light blue fluorescence and the un-dosed wood is represented by the dark blue fluorescence. This image was then processed by splitting the full color image into red, green and blue images. The yellow green fluorescing wood rot had a component in the red and in the green image but virtually none in the blue image. The light blue-fluorescing isocyanate binder had a component in the blue and in the green images but none in the red image. A mask was generated from the monochrome red image using all pixels above a level of 85 on a gray scale of 0–255 to eliminate all wood rot pixels from the green and blue images. The full color image with the masked wood rot is reproduced as FIG. 14. The average image intensity of the unmasked pixels for the blue and green images could then be calculated in the same manner as was used in Example 1. This average image intensity was then correlated to binder dosage. The amount of wood rot could be correlated to the average image intensity of the red image. Additional fluorescing components could be analyzed by examining their red, green and blue images and applying the appropriate image masking techniques or multivariate analysis to each corresponding pixel in the three images.

Although the invention has been described in detail in the foregoing for the purpose of illustration, it is to be understood that detail is solely for that purpose and that variations can be made therein by those skilled in the art without departing from the spirit and scope of the invention except as it may be limited by the claims.

What is claimed is:

1. A process for the production of wood strand board comprising
   a) applying a polyisocyanate to wood strands,
   b) monitoring the polyisocyanate/wood strand material in accordance with a method comprising
      (1) exposing said wood strands to which said polyisocyanate has been applied to ultraviolet waves for a period of time sufficient to cause the said polyisocyanate to fluoresce,
      (2) collecting visible waves emitted by the flourescing polyisocyanate,
      (3) passing the collected ultraviolet waves from (2) through a filter which blocks ultraviolet waves,
      (4) imaging the visible wave emissions of the fluorescing polyisocyanate onto a video camera that converts the image to an electronic signal, and
      (5) relaying the electronic signal generated by the video camera in (4) to a means for correlating dosage and distribution of polyisocyanate to the electronic signal received until the polyisocyanate dosage and distribution are within a previously determined acceptable range,
   c) forming the polyisocyanate/wood strand material into the desired shape or form, and
   d) subjecting the polyisocyanate/wood strand material to curing conditions.

* * * * *